United States Patent [19]

LaGrotta

[11] Patent Number: 4,979,389
[45] Date of Patent: Dec. 25, 1990

[54] METHOD AND APPARATUS FOR DETECTING SURFACE FLAWS IN ELECTRICAL CABLE PLASTIC JACKETING

[75] Inventor: Richard T. LaGrotta, West Orange, N.J.

[73] Assignee: AT&T Bell Laboratories, Murray Hill, N.J.

[21] Appl. No.: 374,371

[22] Filed: Jun. 30, 1989

[51] Int. Cl.$^5$ ............................................. G01M 3/26
[52] U.S. Cl. ................................................ 73/37.700
[58] Field of Search ...................... 73/37.5, 37.6, 37.7, 73/37.8

[56] References Cited

U.S. PATENT DOCUMENTS 2,417,988  3/1947  Mooney ................................. 73/37
2,963,900  12/1960 Kuebler ................................. 73/37
3,402,603  9/1968  Hollister et al. .................... 73/37 X

FOREIGN PATENT DOCUMENTS 5591  1/1977  Japan .................................... 73/37.7

Primary Examiner—Hezron E. Williams
Assistant Examiner—Joseph W. Roskos
Attorney, Agent, or Firm—Charles E. Graves

[57] ABSTRACT

This invention employs principles associated with air-lubricated thrust bearings, to provide highly sensitive indicators of the presence of defects along the surface of a cable insulative layer. A spring-loaded mounted probe containing an axial air passage is closely directed at the cable surface. The cable is moved linearly under the probe, and air is introduced to create air flow at and along the surface in the vicinity of the probe's outlet oriface. The static pressure at the probe outlet oriface is essentially constant, until a surface defect such as a scratch or a protrusion causes a substantial change in the air pressure or air flow rate. The change is detected and recognized as an indication of defect.

12 Claims, 4 Drawing Sheets

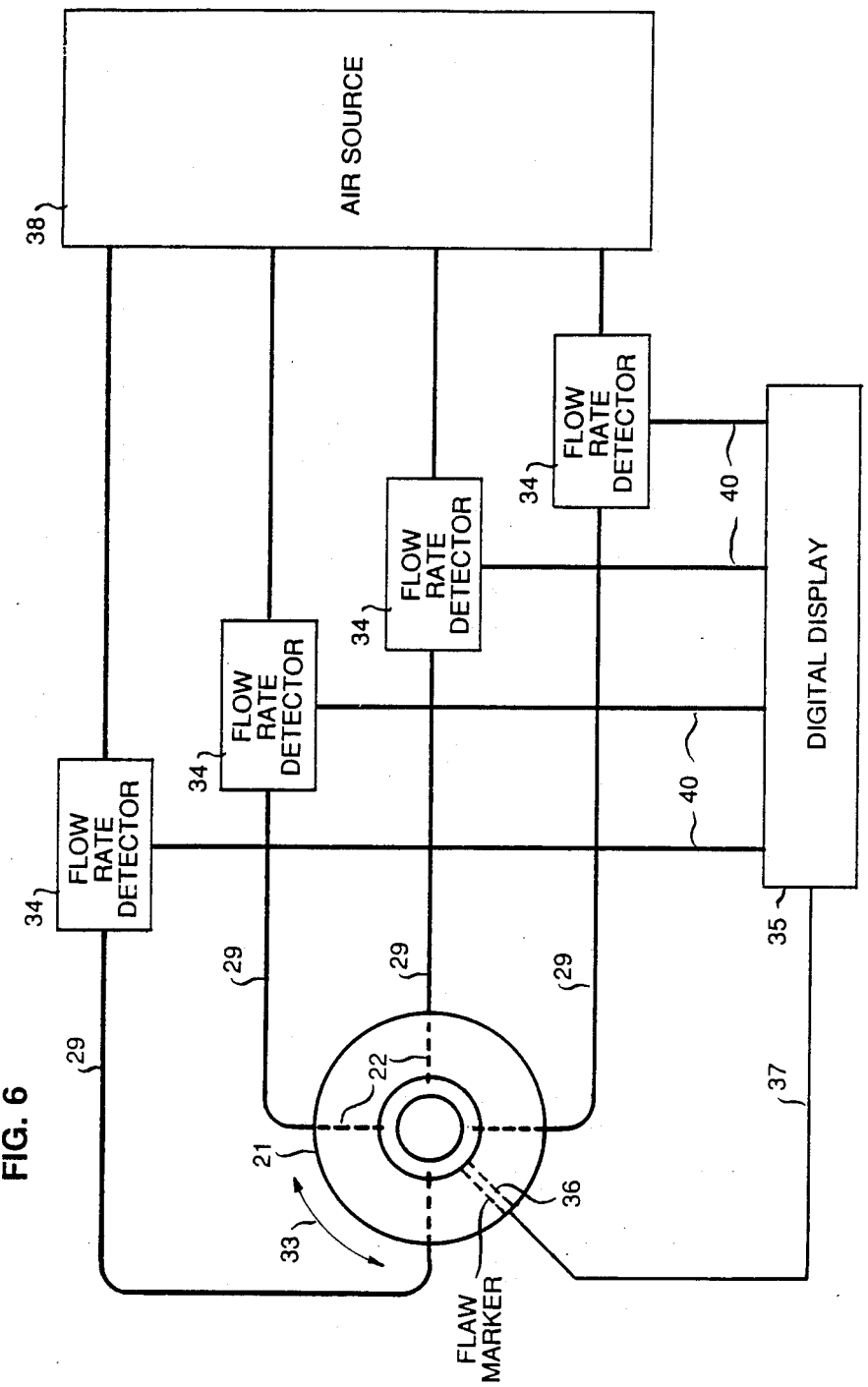

METHOD AND APPARATUS FOR DETECTING SURFACE FLAWS IN ELECTRICAL CABLE PLASTIC JACKETING

This invention was made with Government support under Contract No. N-00039-89-0083 awarded by the Department of the Navy. The government has certain rights in this invention.

FIELD OF THE INVENTION

This invention relates to jacketed cable; and particularly, to the reliable detection of minute surface flaws on the jacket which occur during manufacture.

BACKGROUND OF THE INVENTION

In the manufacture of high reliability long life undersea cable, such as optical fiber telecommunications cable, the integrity of the high voltage insulation is an important factor limiting the life of the cable. One of the variables that affects the integrity of this insulation is surface defects, such as scratches created during manufacture. Increasingly, in both military and commercial applications, a requirement exists that even minute surface defects greater than, for example, 0.005 inches in depth be avoided.

Current techniques used by cable manufacturers to find surface defects on the insulation rely either upon visual inspection or human tactile feel. In the latter case, the inspector literally uses the sensitivity of the hand to detect surface defects.

The current inspection for surface defects thus is very costly because it entails unreeling and re-reeling the cable in a separate process step through an inspection station, at very slow speeds to allow for sufficient manual inspection time. The processes are also inherently inaccurate since they depend on the inspector's subjective interpretation of visual or tactile data. Experience has also shown that it is difficult for an inspector to maintain the necessary accuracy and concentraion during the manual inspection of long lengths of cable.

OBJECTS OF THE INVENTION

One object of the invention is to reduce the instances of surface defects in manufactured cable by devising a reliable and mechanised flaw detection process.

A further object of the invention is to increase the reliability of cable jacket surface flaw detection.

Another object of the invention is to improve the ability of a cable inspector to detect surface flaws without experiencing fatigue and inefficiency.

SUMMARY OF THE INVENTION

This invention makes use of certain principles and physical phenomena associated with air-lubricated thrust bearings, to provide highly sensitive indicators of the presence of defects along the surface of a cable insulative layer such as its outer plastic jacket. Specifically, the invention relies on detecting the variations in pressure or increase in flow rate which occurs when a surface defect passes under an outlet of an air-actuated detection probe stationed over a cable outer jacket. The variations to signal the probable presence of the defect.

In one embodiment of the invention, a spring-loaded probe containing an axial air passage, is closely directed at the cable surface. The cable is moved linearly under the probe. Air is introduced from a regulated pressure source, generating air flow at and along the surface in the vicinity of the probe's outlet orifice. The probe floats a pre-determined distance above the moving surface, suspended by the air pressure. Given a smooth surface, the static pressure at the probe outlet orifice is essentially constant. A surface defect, however, such as a scratch or a protrusion, causes a substantial change in the air flow. The change is detected and recognized as an indication of defect. The cable inspection process includes means for using the air flow or flow rate change data to mark the location of the flawed area for later repair; or alternatively, for repairing the flaw in the next immediate production stage.

Advantageously, a plurality of detector probes are mounted in a ring rigidly disposed around the cable, as the caable is advanced linearly through the ring. By oscillating the probe mounting ring, a substantial fraction of the outer surface of the cable jacket—enough to be statistically significant for flaw detection—is traversed by the probes.

The inspection station containing the present invention advantageously may be included in the cable manufacturing line.

Advantageously, the invention recognizes and utilizes a cubic amplification factor inherent in the gas flow dynamics of the air bearing-suspended probe, because the air flow or pressure varies substantially as the cube of the distance of the probe tip from the valley of a given defect.

The invention, its further objects, features, and advantages will be apparent from a reading of the description to follow of an illustrative embodiment.

DESCRIPTION OF THE DRAWING

FIG. 6 is a schematic block diagram of a control system for the inspection station of FIG. 4.

DETAILED DESCRIPTION OF AN ILLUSTRATIVE EMBODIMENT

1. Theoretical considerations

Figure 1:
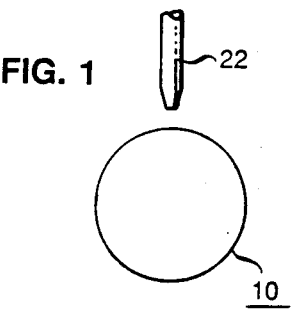
FIG. 1 is schematic diagram of a cable and a probe.

The flow rate of a gas, such as air, in a gas-lubricated hydrostatic thrust bearing varies as the cube of the gas film thickness for a constant pressure and preload. FIG. 1 illustrates the general case, where Q = air volume flow rate
h = gap between a nominal bearing surface and a probe air outlet
X = Viscosity of Air
$P_p$ = air pressure in probe
$P_a$ = atmospheric air pressure
W = pre-load on probe
R = outside diameter of a probe
r = inside diameter of the probe air passage.

The classical relation among these parameters is given by:

$$Q = \frac{\pi h^3}{6X \ln \frac{R}{r}} \left[ \frac{P_p^2 - P_a^2}{2P_a} \right] \quad (1)$$

Figure 3:
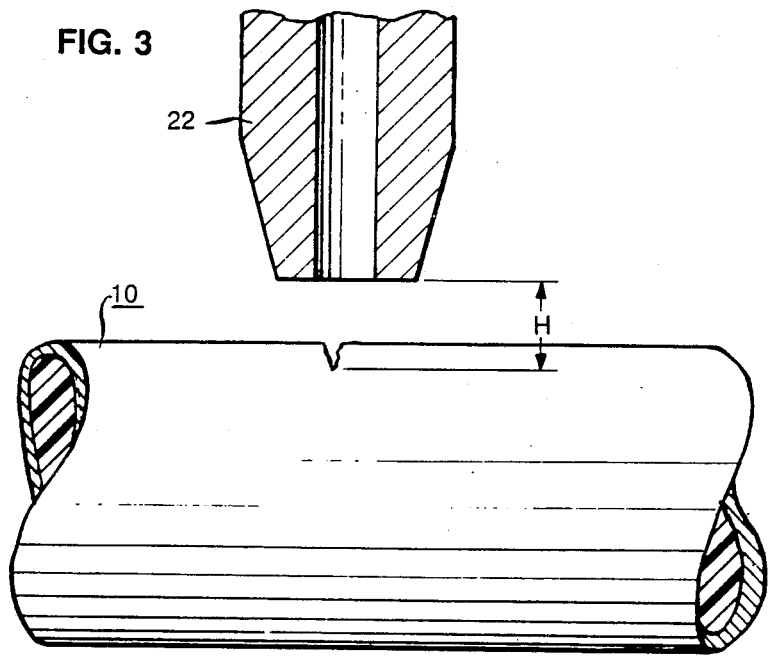

It can be seen from equation 1 that the flow through the probe varies as a cubic function of the gap height h between the probe and the surface. Given a constant air pressure source feeding a probe at a flow rate Q, each time a probe crosses a surface defect, the gap height h increases, effectively affording a greater volume of space beneath the probe, within which air can flow. The greater volume is depicted in FIG. 3, in which the gap height is denoted H. Accompanying the greater volume into which the flowing air can expand, is the additional passage to atmospheric pressure which the defect will afford.

The net effect is that, for a surface scratch, the system experiences a momentary increase in air flow through the passages of the probe. With the travel of the surface defect out from under the probe, a similar perturbation in the system may be experienced. Both perturbations in this illustration are indicia of a surface defect. In the example to follow, it will be shown how the air flow perturbation can be detected and utilized, for example, to mark the location of the defect.

Figure 4:
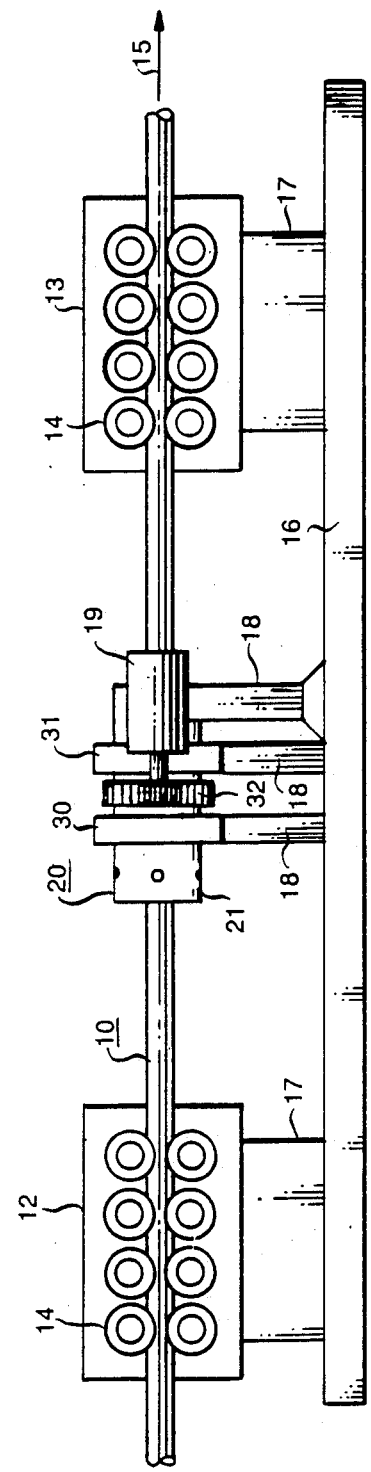
FIG. 4 is schematic side view of a cable flaw inspection station.

The variables which may be controlled in using this approach, are the physical dimensions of the probe, the gap, the air pressure and the pre-load on the probe. FIG. 4 depicts schematically an exemplary defect inspection station using the invention concepts. A cable, 10, having a jacket surface, 11, of extruded polyethylene is transported through the station by a reeling means (not shown) which moves the cable at a set speed in the direction denoted 15. The station components are mounted on a bed, 16. The station may be included as part of a cable production line (not shown). Cable alignment fixtures, 12 and 13, mounted to the bed on stands, 17, serve to steady the cable and move it in a linear motion through rollers, 14, with as little caternary as possible.

Figure 5:
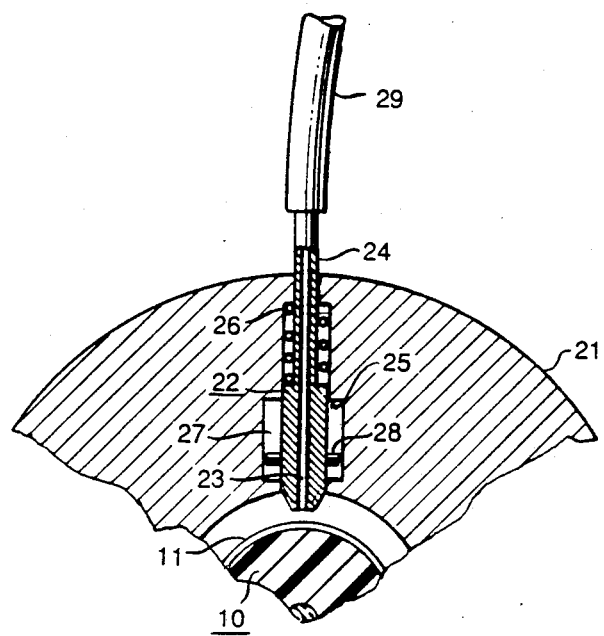
FIG. 5 is a partial frontal view in sectional form of a probe head.
Figure 2:
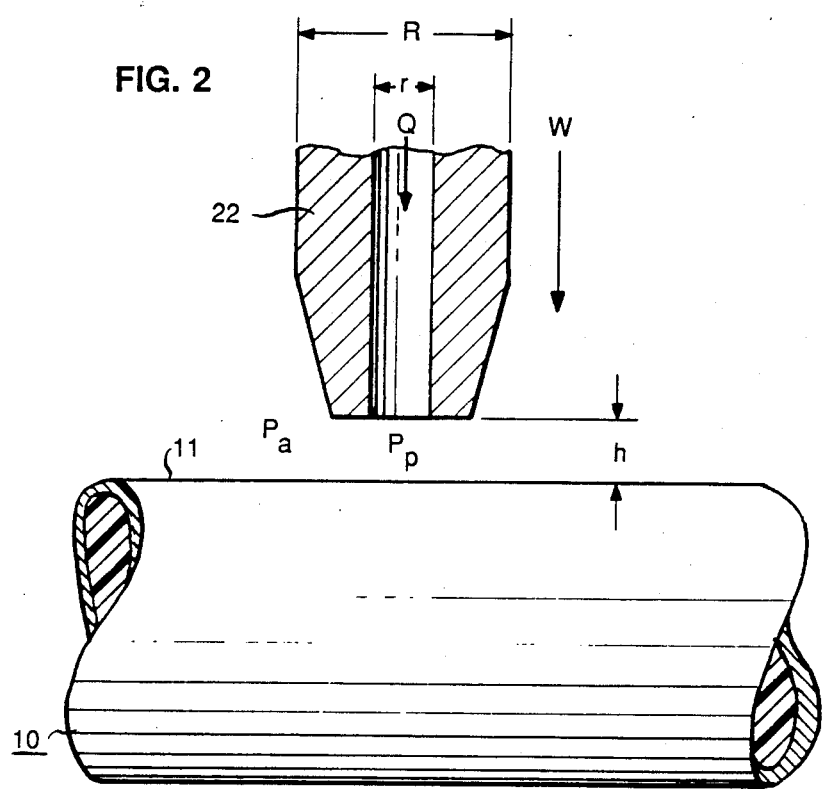
FIGS. 2 and 3 are schematic diagrams of a cable and probe with indicia of parameters included.

The air probe assembly, 20, shown also in FIG. 5, consists of an air probe head, 21, conventionally mounted in a pair of bearings, 30, which in turn are fastened to the bed, 16, with rigid stands, 18. The mounting enables the air probe head to rotate with respect to the linearly-traveling cable, 10, which transits through the head, 21, as shown in FIG. 5, with the cable axis and the head axis substantially coincident. A stepping motor, 19, fixed to bed, 16, drives the probe head, 21, through, for example, a gear arrangement including motordrive gear, 32, and probe head gear, 44, which is conventional and can be constructed in a variety of known configurations.

The probe head, 21, mounts one or, preferably, a plurality of air probes, 22, which in this example number four. As seen in FIG. 5, each probe, 22, consists of an interior air passage, 23, which at its tapered base faces and contacts the underlying cable, 10. Each probe, 22, is mounted to have radial movement toward or away from the cable, 10, by sizing the probe seat, 27 and shaft, 24, appropriately. Probe movement is permitted, by action of the travel pins, 28, connected to the probe body, to assure (in the absence of air pressure) contact with the cable jacket surface, 11, over a wide range of cable diameters.

Each probe, 22, is biased, as with loading spring, 26, which is seated on the probe shaft shoulder, 25, to lightly engage the cable surface in the absence of air pressure. The system allows adjusting of the pre-load on the probe to achieve a desired gap or a desired air flow rate.

An air hose, 29, connects the air passage of each probe, 22, to an air source, 38, schematically depicted in FIG. 6. The air source, 38, should have the capability to supply air to each probe at a constant pressure during the inspection operation. The hoses, 29, which connect the air source, 38, to each probe, 22, are provided with sufficient slack to serve the air probe assembly as the stepper motor rotates the head through, for example, a plus and minus 90 degrees oscillatory motion indicated by arrow, 33.

A probe with an internal air passage 0.050 inches in diameter is able to detect a 0.005 inch scratch. Persons skilled in the art, however, will be able to determined optimum probe geometry and the optimal gap for the probe, depending on the character of the defects anticipated, and the other parameters taught above.

The perturbations in air flow and/or system pressure, described above as occurring in the presence of surface defects, are advantageously detected by conventional flow rate meters, 34, associated with each probe, 22. Connected to each flow rate meter, 34, is a transmission line, 40, feeding a digital readout device, 35. An operator can monitor for defects by observing the perturbations registered on device, 35. Alternatively, device, 35, can be a continuous recording graph (not shown). In either case, it is advantageous to include a marker, 36, mounted as schematically portrayed in FIG. 6, on the air probe head, 21, which responds to indicia of pressure variations, such as pressure drops, and places a visually or otherwise detectable mark onto the cable surface in response to the occurrence of the perturbations.

In constructing the surface flaw detection system pursuant to this invention, it may be desirable to provide the air probe movement with a relatively long time constant. So constructed, the inward movement of each probe will lag somewhat as that probe encounters a defect, thereby allowing more time for the air flow transient to be detected before the system again reaches a stable state.

Desirably, the inside diamater of the air probe passage should be small in relation to the width of any defect; and, practically, should be held to an inside diameter which is only slightly greater than the expected widths of defects.

The system is operated by loading a cable into and through the station, by setting the predetermined loading of the probe onto the cable surface and by supplying air pressure sufficient to commence operation of the probe and cable in the manner of an air bearing system. The oscillation rate and extent (in radians) of oscillation desired, is set into the stepper motor in conventional fashion. The cable is drawn at a rate of, for example, 120 feet per minute through the head, 21. Flaws, which typicaally although not necessarily are in the form of scratches on the surface, 11, register on the meter, 35, and their locations are marked on the cable. In subsequent stations (not shown) the flaw may be repaired.

I claim:

1. Apparatus for detecting defects on the surface of an insulative layer of an electrical cable, comprising:
   means for applying a directed, continuous stream of a gas onto said surface;
   means for monitoring the flow rate of said gas during said application, and for detecting gas flow rate variations; and
   means responsive to detected gas flow rate variations for designating the region of said cable surface to which said gas was applied at time of said flow rate variations.

2. Apparatus for detecting defects on the surface of an insulative layer of a cable, comprising:
  means for linearly transporting said cable;
  one or more probes, each probe comprising
  an internal air passage having an outlet end;
  means for mounting each said probe for movement of said outlet end toward or away from said cable during said transporting;
  said mounting means includinng means for biasing each said probe toward said cable surface;
  means for furnishing air to each said passage, sufficient in pressure and flow rate to lift said probe from said surface;
  means for detecting variations in said pressure of said air flow; and
  means responsive to said detected pressure variations for recording the concurrent location of said probe with respect to said cable.

3. Apparatus for detecting defects on the surface of an insulative layer of a cable, comprising:
  means for linearly transporting said cable;
  one or more probes, each probe comprising
  an internal air passage having an outlet end;
  means for mounting each said probe for movement of said outlet end toward or away from said cable surface during said transporting;
  said mounting means including means for biasing each said probe toward said cable surface;
  means for furnishing air to each said passage, sufficient in pressure and flow rate to lift said probe from said surfce, thereby to create a gap between said probe and said surface when said surface beneath said probe is substantially of constant radius;
  means responsive to deviations from said contant cable surface radius occurring beneath said probe, for detecting resulting variations in said pressure or said flow rate; and
  means responsive to said detected variations for recording the location of said probe with respect to said cable at the time.

4. Apparatus in accordance with claims 2 or 3, wherein said recording means comprises:
  means for placing a detectable mark onto the cable surface at the time of a said detected variation of air flow or of air pressure.

5. Apparatus in accordance with claim 4, wherein said variation detection means comprises an air flow rate meter.

6. Apparatus in accordance with claim 4, wherein said air furnishing means further comprises means for supplying air to each probe at a substantially constant pressure.

7. Apparatus in accordance with claim 4, further comprising
  means for rotating said probes with respect to the axis of said cable as said cable advances through said probes.

8. Apparatus in accordance with claim 7, wherein said rotating means comprises means for producing an oscillatory movement of said probes with respect to said cable surface, with a preselected periodicity.

9. A process for detecting defects in a substantially circular cross-section surface of a plastic jacket surrounding a cable, comprising the steps of:
  applying a continuous stream of a gas at an elevated and substantially constant pressure onto said surface;
  monitoring the flow rate of said gas during said application;
  detecting gas flow rate variations; and
  designating the region of said cable surface to which said gas was applied at time of said flow rate variation.

10. A process for detecting defects in a substantially circular cross-section surface of a plastic jacket surrounding a cable, comprising the steps of:
  moving said cable linearly through a detection station;
  applying a continuous stream of a gas at an elevated and substantially constant pressure onto said surface, from one or more probes, each probe comprising an internal air passage having an outlet end, said stream being sufficient in pressure and flow rate to lift said probe from said surface;
  detecting variations in said pressure or said gas flow rate; and
  recording the location of said probe with respect to said cable surface at the time of occurrence of said pressure or flow rate variations.

11. The process of claim 9 or claim 10, comprising the further step of:
  oscillating said probes with respect to said surface.

12. The process of claim 11, wherein said recording step comprises placing a detectable mark onto said cable surface at the time of a said detected variation in pressure or flow rate.

* * * * *

UNITED STATES PATENT AND TRADEMARK OFFICE
CERTIFICATE OF CORRECTION

PATENT NO. : 4,979,389
DATED : December 25, 1990
INVENTOR(S) : Richard T. LaGrotta It is certified that error appears in the above-identified patent and that said Letters Patent is hereby corrected as shown below:

Column 1, line 63 - change "The variations to signal the" to
--The variations signal the--.

Column 2, line 38 - change "cable flaw" to --cable surface flow--;

Column 2, line 55 - change "Viscosity of Air" to --viscosity of air--.

Column 3, line 23 - change "approach," to --approach--;

Column 3, line 43 - change "travelying" to --traveling--.

Column 5, line 40 - change "contant" to --constant--.

Signed and Sealed this

Twenty-eighth Day of July, 1992

Attest:

DOUGLAS B. COMER

*Attesting Officer*     *Acting Commissioner of Patents and Trademarks*